United States Patent [19]
Beauquey et al.

[11] Patent Number: 5,916,549
[45] Date of Patent: *Jun. 29, 1999

[54] DETERGENT COSMETIC COMPOSITIONS FOR HAIR USE AND THE USE THEREOF

[75] Inventors: Bernard Beauquey, Clichy; Daniele Cauwet, Paris; Sandrine DeCoster, Epinay Sur Seine; Claude DuBief, Le Chesnay, all of France

[73] Assignee: L'Oréal, S.A., France

[*] Notice: This patent issued on a continued prosecution application filed under 37 CFR 1.53(d), and is subject to the twenty year patent term provisions of 35 U.S.C. 154(a)(2).

[21] Appl. No.: 08/866,077

[22] Filed: May 30, 1997

Related U.S. Application Data

[63] Continuation of application No. 08/362,847, Dec. 22, 1994, abandoned.

[30] Foreign Application Priority Data

Jan. 11, 1994 [FR] France ................................ 94 00220

[51] Int. Cl.$^6$ ............................ A61K 7/06; A61K 7/075; A61K 7/50
[52] U.S. Cl. ................................. 424/70.19; 424/70.21; 424/70.22; 510/126
[58] Field of Search ............................ 424/70.11, 70.12, 424/70.19, 70.21, 70.22; 252/173, DIG. 13, DIG. 14, DIG. 7; 510/119, 126

[56] References Cited

U.S. PATENT DOCUMENTS

| | | | |
|---|---|---|---|
| 3,836,537 | 9/1974 | Boerwinkle et al. | |
| 4,217,914 | 8/1980 | Jacquet et al. | |
| 4,445,521 | 5/1984 | Cauwet et al. | |
| 4,479,893 | 10/1984 | Hirota et al. | 252/542 |
| 4,839,166 | 6/1989 | Dubief et al. | |
| 4,971,784 | 11/1990 | Hölzel et al. | 424/70.1 |
| 4,996,059 | 2/1991 | Cauwet et al. | |
| 5,009,813 | 4/1991 | Watanabe et al. | |
| 5,089,252 | 2/1992 | Dubief et al. | |
| 5,137,715 | 8/1992 | Hoshowski et al. | 424/70 |
| 5,254,336 | 10/1993 | Hoshowski et al. | 424/70.1 |
| 5,332,581 | 7/1994 | Yoshihara et al. | 424/70.1 |
| 5,391,368 | 2/1995 | Gerstein | 424/70.13 |
| 5,403,517 | 4/1995 | Horinishi et al. | 424/70.1 |
| 5,476,649 | 12/1995 | Naito et al. | 424/70.1 |
| 5,523,017 | 6/1996 | Moran et al. | 252/174.21 |
| 5,540,853 | 7/1996 | Trinh et al. | 510/107 |
| 5,575,991 | 11/1996 | Kischka et al. | 424/70.2 |
| 5,607,678 | 3/1997 | Moore et al. | 424/401 |
| 5,612,301 | 3/1997 | Inman | 510/122 |
| 5,641,479 | 6/1997 | Linares et al. | 424/70.21 |
| 5,665,336 | 9/1997 | Wolfram | 424/70.6 |
| 5,685,882 | 11/1997 | Samain et al. | 8/408 |

FOREIGN PATENT DOCUMENTS

| | | |
|---|---|---|
| A-0269243 | 6/1988 | European Pat. Off. |
| A-0337354 | 10/1989 | European Pat. Off. |
| A-0398177 | 11/1990 | European Pat. Off. |
| A-0403304 | 12/1990 | European Pat. Off. |
| A-0413528 | 2/1991 | European Pat. Off. |
| 437 114 | 7/1991 | European Pat. Off. |
| A-0492657 | 7/1992 | European Pat. Off. |
| A-0508324 | 10/1992 | European Pat. Off. |
| 531943 A1 | 3/1993 | European Pat. Off. |
| 2091516 | 1/1972 | France |
| 2270846 | 1/1976 | France |
| 2383660 | 10/1978 | France |
| 2470596 | 6/1981 | France |
| 2519863 | 7/1983 | France |
| 2598611 | 11/1987 | France |
| 2-218797 | 8/1990 | Japan |
| 3-034914 | 2/1991 | Japan |
| WO 93/15711 | 8/1993 | WIPO |

OTHER PUBLICATIONS

R.G. Lomax, "Balanced Amphoteric Surfactants," Soap Cosmetics Chemical Specialties, vol. 48, No. 11, pp. 29–32, 66 (1972).

Derwent Abstract of French Pat. App. FR 2,091,516, Jan. 14, 1972.

*Primary Examiner*—Robert H. Harrison
*Attorney, Agent, or Firm*—Finnegan, Henderson, Farabow, Garrett, & Dunner, LLP

[57] ABSTRACT

Novel detergent hair compositions (shampoos) which are more particularly suitable for so-called sensitized hair, the compositions comprising a cosmetically acceptable medium containing at least one anionic surface-active agent, at least one imidazoline amphoteric surface-active agent, at least one conditioning agent, and at least 1% by weight relative to the total weight of the composition of at least one carboxylic acid having a hydroxyl radical in the α-position (alpha-hydroxy acid) or a derivative thereof. The compositions make it possible to obtain hair which, after washing, has enhanced lightness, smoothness, shine and mechanical strength.

27 Claims, No Drawings

DETERGENT COSMETIC COMPOSITIONS FOR HAIR USE AND THE USE THEREOF

This is a continuation of application Ser. No. 08/362,847, filed Dec. 22, 1994, now abandoned.

The present invention relates to novel cosmetic compositions, having enhanced properties, intended for the cleaning or care of the hair and/or the scalp, based on anionic surfactants, specific amphoteric surfactants, conditioning agents and α-hydroxylated carboxylic acids or their derivatives, as well as their use in this cosmetic application.

For the cleaning and/or care of the hair, it is common to use detergent hair compositions, or shampoos, containing both anionic surface-active agents and amphoteric surface-active agents (mixtures). Indeed, it is known that these compositions possess excellent washing power, but the intrinsic cosmetic properties associated with them still remain relatively low.

Therefore, in order to enhance the cosmetic properties of the above detergent compositions and more particularly of those which are destined for application to sensitized hair, i.e., hair which is damaged or rendered fragile in particular under the chemical action of atmospheric agents and/or of hair treatments such as permanent waves, dyeing or bleaching, it is known to introduce into these compositions complementary cosmetic agents known as conditioning agents, in particular polymers, for example, such as cationic polymers, amphoteric polymers or alternatively silicones and/or silicone derivatives, which then provide the treated hair with a markedly improved facility for untangling and styling and markedly improved softness.

However, in the particular case where, for the production of the detergent composition based on anionic and amphoteric surfactants and conditioning agents, use is made of amphoteric surface-active agents of the imidazoline type, it is observed, in a manner which cannot be explained, that the cosmetic advantages mentioned above are unfortunately also accompanied, on dried hair, by certain cosmetic effects deemed to be undesirable, namely lankness of the hairstyle (lack of lightness of the hair), lack of smoothness (non-homogeneous hair from the root to the tip) and insufficient shine. Moreover, it is observed that these drawbacks are greatly accentuated in the case of application of the detergent composition to sensitized hair; in addition, if the hair has been sensitized by dyeing treatments, in particular by oxidation dyes, the repeated use of the detergent composition induces in the long run a harmful decrease in the mechanical strength of the hair.

In summary, the current detergent compositions containing anionic surfactants, amphoteric surfactants of the imidazoline type, and conditioning agents do not give complete satisfaction.

After considerable research conducted in this matter, it has been found by the inventors that by introducing, in a sufficient amount, α-hydroxylated carboxylic acids or their derivatives into the detergent hair compositions of the prior art based on anionic surfactants, amphoteric surfactants of the imidazoline type and conditioning agents, it is possible to limit, or even to eliminate altogether, the problems generally associated with the use of such compositions, namely in particular the lankness, the lack of smoothness and shine, and the lessening in mechanical strength of the hair, while at the same time conserving the washing power and the other advantageous cosmetic properties (softness, untangling, styling) which are associated with these compositions. This discovery forms the basis of the present invention.

Thus, according to the present invention, there are now proposed novel detergent hair compositions comprising a cosmetically acceptable medium containing at least one anionic surface-active agent, at least one amphoteric surface-active agent of imidazoline type, at least one conditioning agent, and at least 1% by weight relative to the total weight of the composition of at least one carboxylic acid having a hydroxyl radical in the α position or a derivative thereof. Derivatives of α-hydroxy acid, as defined herein, are salts and/or lactides of α-hydroxy acid.

Another subject of the invention is the use in cosmetics of the above compositions for the cleaning or care of the hair and/or of the scalp.

Other characteristics, aspects and advantages of the invention will emerge more clearly on reading the description which will follow and the concrete, but in no way limiting, examples intended to illustrate it.

According to the present invention, and in accordance with the definition recognized in the state of the art (see in particular in this regard, "Handbook of Surfactants" by M. R. Porter, Blackie & Son (Glasgow and London), 1991, pp. 199–202, the disclosure of which is hereby incorporated by reference), amphoteric surfactant of imidazoline type is understood to refer to any amphoteric surfactant capable of being prepared by mono- or dicarboxylation (in particular by chloroacetylation and/or chloropropionylation) of an alkyl- or alkenylamidoethylaminoethanol of general formula $RCONHCH_2CH_2NHCH_2CH_2OH$, in which R denotes a saturated or unsaturated hydrocarbon radical which is generally derived from a fatty acid (the latter compound being, in fact, generally obtained by reaction between a fatty acid and aminoethylaminoethanol)

The amphoteric surfactants of imidazoline type more particularly targeted by the present invention correspond to the following general formula (I)

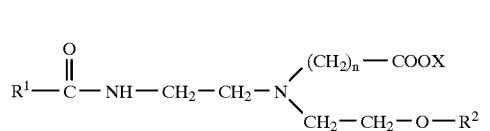

in which:

R¹ represents a saturated or unsaturated hydrocarbon radical, such as a fatty acid residue, R² represents a hydrogen atom or the group —$(CH_2)_m$—COOY, X and Y represent, independently or simultaneously, a hydrogen atom or a monovalent cation, especially a metal cation and in particular a cation of an alkali metal such as sodium, n and m are two integers which may, independently or simultaneously, be equal to 1 or 2.

The amphoteric surfactants of formula (I) above which fall particularly well into the scope of the present invention are those having at least one, and preferably more than one, of the following characteristics: n and m are identical; R² represents the group —$(CH_2)_m$—COOY; X and Y are identical and preferably represent a monovalent metal cation, in particular of sodium; R¹ represents an alkyl radical which is generally $C_5$–$C_{20}$, in particular a $C_7$, $C_9$, $C_{11}$, $C_{13}$ or $C_{17}$ alkyl radical, a $C_{17}$ unsaturated radical, or alternatively an alkyl radical of an acid R¹—COOH present in natural oils, such as in those of coconut, copra, linseed, wheat germ or animal tallow.

By way of concrete examples of amphoteric surfactants of imidazoline type, there may in particular be mentioned those sold under the general trade name of MIRANOL® by the company Rhone Poulenc, as well as those having the following CTFA definitions (CTFA dictionary, 4th edition, 1991): disodium caproamphodiacetate, disodium caproamphodipropionate, disodium capryloamphodiacetate, disodium capryloamphodipropionate, disodium cocoamphodiacetate, disodium cocoamphodipropionate, disodium isostearoamphodiacetate, disodium isostearoamphodipropionate, disodium lauroamphodiacetate, disodium lauroamphodipropionate, disodium oleoamphodipropionate, disodium stearoamphodiacetate, disodium tallow amphodiacetate and disodium wheat germ amphodiacetate.

It will be noted here that the general cosmetic problems recounted at the start of the description, associated with the use of detergent compositions containing anionic surfactants and conditioners in combination with amphoteric surfactants of imidazoline type (lankness, smoothness, shine and mechanical strength), are found to be particularly exacerbated when the said amphoteric surfactants of imidazoline type are, according to the CTFA nomenclature, disodium cocoamphodiacetates or disodium cocoamphodipropionates.

The detergent compositions in accordance with the invention may, of course, contain one or more amphoteric surface-active agents as above.

The nature of the anionic surfactant entering into the detergent compositions according to the invention is not critical. Thus, anionic surfactants which may be used, alone or as mixtures, in the context of the present invention, include, but are not limited to the salts (in particular the alkali metal salts, especially of sodium, ammonium salts, amine salts, amino alcohol salts or magnesium salts) of the following compounds: alkyl sulphates, alkyl ether sulphates, alkylamidoether sulphates, alkylarylpolyether sulphates and monoglyceride sulphates; alkyl sulphonates, alkyl phosphates, alkyl amide sulphonates, alkyl arylsulphonates, $\alpha$-olefin sulphonates and paraffin sulphonates; alkyl sulphosuccinates, alkyl ether sulphosuccinates and alkyl amide sulphosuccinates; alkyl sulphosuccinamates; alkyl sulphoacetates; alkyl ether phosphates; acyl sarcocinates and N-acyltaurates, the alkyl or acyl radical of all these various compounds preferably containing from 12 to 20 carbon atoms. Among the anionic surfactants which may also be used, there may equally be mentioned fatty acid salts such as the salts of oleic acid, ricinoleic acid, palmitic acid and stearic acid, the acids of copra oil or of hydrogenated copra oil; acyl lactates in which the acyl radical contains 8 to 20 carbon atoms. It is also possible to use weakly anionic surfactants, such as the alkyl D-galactoside uronic acids and their salts, as well as polyoxyalkylenated carboxyl ethers, in particular those containing from 2 to 24 ethylene oxide groups, and their mixtures.

The conditioning agents which may be used in the context of the present invention may be chosen from all those already known per se as enhancing the cosmetic properties of hair treated with detergent compositions, namely in particular cationic polymers, such as those described, for example, in European Patent Application EP-A-O,337,354 and in French Patent Applications FR-A-2,270,846, FR-A-2,383,660, FR-A-2,598,611, FR-A-2,470,596 and FR-A-2,519,863, the entire disclosures of which are hereby incorporated by reference; amphoteric polymers such as those described, for example, in European Patent Application EP-A-0,269,243 and U.S. Pat. No. 3,836,537, the entire disclosures of which are hereby incorporated by reference, and the last two French Patent Applications cited above; silicones and their derivatives, such as those described, for example, in European Patent Applications EP-A-0,398,177 and EP-A-0,492,657, the entire disclosures of which are hereby incorporated by reference, and, although to a far lesser extent, certain anionic polymers. It is, of course, possible to use mixtures of conditioners.

According to an essential characteristic of the detergent hair compositions according to the invention, these compositions contain at least one carboxylic acid which is hydroxylated in the $\alpha$ position (which compound is also referred to as an $\alpha$-(alpha) hydroxy acid) or a derivative thereof. Acid derivatives, as defined herein, are associated salts (salts with organic bases or alkali metal for example) or lactides (obtained, for example, by autoesterification of $\alpha$-hydroxy acid molecules).

This $\alpha$-hydroxy acid may obviously consist of a mono- or polycarboxylic acid containing one or more hydroxyl functions, at least one of these hydroxyl functions necessarily occupying a position $\alpha$ to the said acid (carbon adjacent to a carboxylic function). This acid may be present in the final detergent composition in free acid form and/or in the form of one of its combined salts (salts with an organic base or with an alkali metal in particular, depending in particular on the final pH imposed on the composition, or alternatively possibly in the form of the corresponding lactide (obtained, for example, by autoesterification of the molecules). The detergent compositions in accordance with the invention may, of course, contain one or more $\alpha$-hydroxy acids or their derivatives. Preferably, the $\alpha$-hydroxy acid is selected from linear $\alpha$-hydroxy acids with less than 5 carbon atoms and aromatic $\alpha$-hydroxy acids. Examples of such compounds include, among others, citric acid, lactic acid, methyllactic acid, phenyllactic acid, malic acid, mandelic acid, glycolic acid, tartronic acid, tartaric acid, gluconic acid, benzylic acid and 2-hydroxycaprylic acid. Other compounds of $\alpha$-hydroxy acid type suitable for the present invention are those cited in European Patent Application EP-A-0,413,528, the disclosure of which, in this regard, is hereby incorporated by reference.

The acids which are cosmetically compatible with and acceptable for the hair, the skin and/or the scalp will preferably be chosen.

According to a particularly preferred embodiment of the present invention, the $\alpha$-hydroxy acid used is chosen from citric acid, lactic acid and tartaric acid.

According to another important characteristic of the detergent compositions according to the invention, the $\alpha$-hydroxy acid or acids are present in these compositions in amounts of at least 1% by weight, preferably at least 2% by weight, more preferably at least 3% by weight, relative to the whole of the composition. More preferably, the $\alpha$-hydroxy acid content ranges from 1 to 10% by weight, still more preferably from 2 to 10% by weight, and even more preferably from 4 to 5% by weight. It will be noted that these concentrations are markedly higher than those which are sometimes encountered in shampoos of the prior art when certain acids have been employed solely for the purposes of adjusting the pH.

In yet another embodiment of the present invention, the ingredients in the detergent hair composition, i.e., the anionic surface-active agent, the imidazoline amphoteric surface-active agent, the conditioning agent, and the $\alpha$-hydroxy acid) or its derivative, are present in the detergent hair composition in an amount effective for treating hair to enhance one or more cosmetic properties selected from lightness, smoothness and shine, relative to hair treated with another detergent hair composition identical to the detergent hair composition except lacking the at least one carboxylic acid but brought to the same pH by the addition of hydrochloric acid.

As a guide, the detergent formulations in accordance with the invention generally have the following compositions:

(i) anionic surfactant(s): from 5 to 50% by weight, preferably from 5 to 20% by weight, relative to the total weight of the detergent formulation;

(ii) amphoteric surfactant(s): from 10 to 70% by weight and preferably from 30 to 60% by weight relative to the total weight of the anionic surfactant or surfactants present in the detergent formulation;

(iii) conditioning agent(s) from 0.01 to 10% relative to the total weight of the detergent formulation:

(iv) α-hydroxy acid(s): as indicated above.

The vehicle or support, defined herein as a cosmetically acceptable medium, for the detergent compositions according to the invention is preferably an aqueous medium such as water, or an aqueous-alcoholic solution of a lower alcohol such as ethanol, isopropanol or butanol.

The detergent compositions according to the invention have a final pH which preferably ranges from 2 to 8. More preferably, this pH ranges from 3 to 7. Adjustment of the pH to the desired value may be carried out conventionally by addition of a base (organic or inorganic) to the composition, for example of aqueous ammonia or a primary, secondary or tertiary (poly)amine such as monoethanolamine, diethanolamine, triethanolamine, isopropanolamine or 1,3-propanediamine. Aqueous ammonia is preferably used. Neutralization of the α-hydroxy acid by a base has the supplementary advantage of favoring formation of a buffer which, by avoiding fluctuations in pH, enables the stability of the shampoo to be enhanced; moreover, this neutralization generally causes a spontaneous thickening of the shampoo, which is often sought in this type of application.

The detergent compositions according to the invention may, of course, additionally contain all the usual adjuvants encountered in the field of shampoos, for example such as fragrances, preserving agents, sequestering agents, thickening agents (PEG and PEG derivatives in particular), softening agents, foam modifiers, dyes, pearling agents, moisturizing agents, anti-dandruff or anti-seborrhoeia agents, vitamins, sunscreen agents and others.

These compositions may be provided in the form of liquids which are thickened to a greater or lesser extent, creams or gels, and they are mainly suitable for the washing, the care and/or the beauty of the hair.

Concrete examples illustrating the invention will now be given. It is to be understood that these examples are merely illustrative and not limiting.

EXAMPLE

Three shampoos in accordance with the invention (A, B and C), which had the following compositions, were prepared and tested:

Shampoo A:

| | |
|---|---|
| - Sodium lauryl ether sulphate containing 2.2 mol of ethylene oxide (anionic surfactant) | 7.28 g |
| - Disodium ricinoleyl monoethanolamide sulphosuccinate, sold under the name REWORDEM S 1333 by REWO (anionic surfactant) | 0.8 g |
| - Sodium cocoamidoethyl-(N-hydroxy ethyl-N-carboxymethyl) glycinate, sold under the name MIRANOL C2M by RHONE-POULENC (imidazoline-type amphoteric surfactant) | 3.8 g |
| - Cross-linked and quaternized hydroxy ethyl cellulose, sold under the name JR 400 by the company UNION CARBIDE (conditioning agent) | 0.1 g |
| - Copra acid monoisopropanolamide (thickening agent) | 1.5 g |
| - EDTA | 0.39 g |
| - Preserving agents | 0.31 g |
| - Citric acid | 5 g |
| - Water | qs 100 g |

The pH of this shampoo was adjusted to pH 4.5 by addition of aqueous ammonia.

Shampoo B:

| | |
|---|---|
| - Triethanalamine lauryl sulphate (anionic surfactant) | 10 g |
| - Disodium lauryl monosulphosuccinate, sold under the name SETACIN F SPECIAL PASTE by ZSCHIMMER SCHWARTZ (anionic surfactant) | 0.8 g |
| - Sodium cocoamidoethyl (N-hydroxyethyl N-carboxymethyl) glycinate (imidazoline-type amphoteric surfactant) | 1.14 g |
| - Cross-linked and quaternized hydroxy ethyl cellulose, sold under the name JR 400 by the company UNION CARBIDE (conditioning agent) | 0.2 g |
| - Vinylpyrrolidone/dimethylaminoethyl methacrylate copolymer quaternized with diethyl sulphate, sold under the name GAFQUAT 755 by the company ISP (conditioning agent) | 0.2 g |
| - EDTA | 0.26 g |
| - Preserving agents | 0.11 g |
| - Citric acid | 5 g |
| - Water | qs 100 g |

The pH of this shampoo was adjusted to pH 5 by addition of aqueous ammonia.

Shampoo C:

| | |
|---|---|
| - Monoethanolamine lauryl ether sulphate containing 2.2 mol of ethylene oxide, sold under the name SIPON LEM 235 by HENKEL (anionic surfactant) | 15.4 g |
| - Sodium cocoamidoethyl-(N-hydroxyethyl N-carboxymethyl) glycinate (imidazoline-type amphoteric surfactant) | 1.14 g |
| - Cross-linked and quaternized hydroxy ethyl cellulose, sold under the name JR 400 by the company UNION CARBIDE (conditioning agent) | 0.15 g |
| - EDTA | 0.5 g |
| - Preserving agents | 0.31 g |
| - Citric acid | 5 g |
| - Water | qs 100 g |

The pH of this shampoo was adjusted to pH 5 by addition of aqueous ammonia.

The cosmetic performance of the above shampoos was assessed by a panel of experts using sensory analysis tests conducted in vivo on sensitized human hair (in this case, permanent-waved hair). The procedure was as follows: the shampoos were applied to wet hair, then emulsified and finally rinsed with water after being left on the hair for a few minutes; after drying, the hair was examined by the experts.

As a comparison, three compositions A', B' and C' identical respectively to the compositions A, B and C above were also tested, according to the same procedure, the only difference being that this time all three lacked α-hydroxy acids and that they were brought to the same pH as that of the corresponding compositions of the invention by addition of hydrochloric acid.

The panel of experts judged and concluded that the compositions A, B and C in accordance with the invention had, relative to the corresponding comparative compositions, the following representative beneficial effects: provision of lightness, suppleness, smoothness and shine to dry hair.

Moreover, mechanical strength tests conducted on hair which had been repeatedly treated several tens of times with the comparative shampoos, on the one hand, and the shampoos in accordance with the invention, on the other hand, showed that, in this latter case, there was no appreciable loss of mechanical strength of the hair.

What is claimed is:

1. A detergent hair composition comprising a cosmetically acceptable medium containing:
   (a) at least one anionic surface-active agent;
   (b) at least one imidazoline amphoteric surface-active agent;
   (c) at least one conditioning agent; and
   (d) at least 2% by weight relative to the total weight of the composition of at least one carboxylic acid having a hydroxyl radical in the α position (alpha-hydroxy acid) or a salt or a lactide thereof;
   wherein the at least one imidazoline amphoteric surface-active agent is a compound of formula (I):

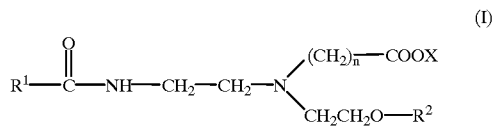

in which:
   $R^1$ represents a saturated or unsaturated hydrocarbon radical,
   $R^2$ represents a hydrogen atom or the group —$(CH_2)_m$—COOY,
   X and Y represent, independently or simultaneously, a hydrogen atom or a monovalent cation,
   n is an integer equal to 1 or 2 and
   m is an integer equal to 1 or 2.

2. A composition according to claim 1, wherein said at least one carboxylic acid or its salt or lactide is present in an amount of at least 3% by weight.

3. A composition according to claim 1, wherein said at least one carboxylic acid or its salt or lactide is present in an amount of less than 10% by weight.

4. A composition according to claim 1, wherein the anionic surfactant or surfactants are present in an amount of from 5 to 50% by weight relative to the total weight of the composition.

5. A composition according to claim 4, wherein the anionic surfactant or surfactants are present in an amount of from 5 to 20% by weight relative to the total weight of the composition.

6. A composition according to claim 1, wherein the amphoteric surfactant or surfactants are present in an amount of from 10 to 70% by weight relative to the total weight of the anionic surfactant or surfactants.

7. A composition according to claim 6, wherein the amphoteric surfactant or surfactants are present in an amount of from 30 to 60% by weight relative to the total weight of the anionic surfactant or surfactants.

8. A composition according to claim 1, wherein the conditioning agent or agents are present in an amount of from 0.01 to 10% by weight relative to the total weight of the composition.

9. A composition according to claim 1, wherein the composition is an aqueous or aqueous-alcoholic composition.

10. A composition according to claim 1, wherein the composition has a pH which ranges from 2 to 8.

11. A composition according to claim 10, wherein said pH ranges from 3 to 7.

12. A composition according to claim 1, wherein the alpha-hydroxy acid is present in free acid form and/or in the form of one of its combined salts and/or in the form of the corresponding lactide.

13. A composition according to claim 1, wherein the alpha-hydroxy acid is selected from citric acid, lactic acid, and tartaric acid.

14. A composition according to claim 1, wherein the conditioning agent is selected from cationic polymers, amphoteric polymers, silicones and silicone derivatives.

15. A composition according to claim 1, wherein said monovalent cation is a metal cation and wherein $R^1$ is a fatty acid residue.

16. A composition according to claim 15, wherein said metal cation is a cation of an alkali metal.

17. A composition according to claim 16, wherein said alkali metal is sodium.

18. A composition according to claim 1, wherein n and m are identical; $R^2$ represents the group —$(CH_2)_m$—COOY; X and Y are identical and represent a monovalent metal cation; $R^1$ represents a $C_5$–$C_{20}$ alkyl radical or a $C_{17}$ unsaturated radical, or an alkyl radical of an acid $R^1$—COOH present in natural oils.

19. A composition according to claim 18, wherein said metal cation is a sodium metal cation; wherein $R^1$ represents a $C_7$, $C_9$, $C_{11}$, $C_{13}$ or $C_{17}$ alkyl radical; and wherein the alkyl radical of an acid $R^1$—COOH is selected from said acid present in coconut oil, copra oil, linseed oil, wheat germ oil and animal tallow.

20. A composition according to claim 18, wherein the at least one imidazoline amphoteric surfactant is selected from disodium cocoamphodiacetates and disodium cocoamphodipropionates (CTFA nomenclature).

21. A process for cleaning and/or care of the hair and/or the scalp comprising applying to said hair and/or scalp an effective amount of a composition as defined in claim 1.

22. A process according to claim 21, wherein said hair is sensitized hair.

23. A detergent hair composition comprising a cosmetically acceptable medium containing:
   (a) at least one anionic surface-active agent;
   (b) at least one imidazoline amphoteric surface-active agent;
   (c) at least one conditioning agent; and
   (d) at least one carboxylic acid having a hydroxyl radical in the α position (alpha-hydroxy acid) or a salt or a lactide thereof,
   wherein the at least one imidazoline amphoteric surface-active agent is a compound of formula (I):

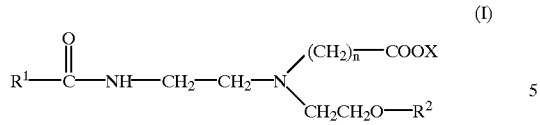

in which:
R¹ represents a saturated or unsaturated hydrocarbon radical,
R² represents a hydrogen atom or the group —(CH$_2$)$_m$—COOY,
X and Y represent, independently or simultaneously, a hydrogen atom or a monovalent cation,
n is an integer equal to 1 or 2 and
m is an integer equal to 1 or 2, said ingredients being present in said detergent hair composition in an amount effective for treating sensitized hair without substantially reducing the mechanical strength of said hair.

24. A detergent hair composition comprising a cosmetically acceptable medium containing:
(a) at least one anionic surface-active agent;
(b) at least one imidazoline amphoteric surface-active agent;
(c) at least one conditioning agent; and
(d) at least one carboxylic acid having a hydroxyl radical in the α position (alpha-hydroxy acid) or a salt or a lactide thereof,
wherein the at least one imidazoline amphoteric surface-active agent is a compound of formula (I):

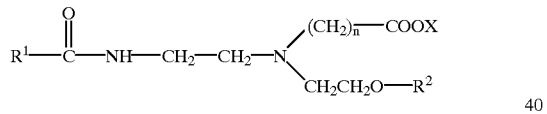

in which:
R¹ represents a saturated or unsaturated hydrocarbon radical,
R² represents a hydrogen atom or the group —(CH$_2$)$_m$—COOY,
X and Y represent, independently or simultaneously, a hydrogen atom or a monovalent cation,
n is an integer equal to 1 or 2 and
m is an integer equal to 1 or 2, said ingredients being present in said detergent hair composition in an amount effective for treating hair to enhance one or more cosmetic properties selected from lightness, smoothness and shine.

25. A detergent hair composition comprising a cosmetically acceptable medium containing:
(a) at least one anionic surface-active agent;
(b) at least one imidazoline amphoteric surface-active agent;
(c) at least one conditioning agent; and
(d) at least 1% by weight relative to the total weight of the composition of at least one carboxylic acid having a hydroxyl radical in the α position (alpha-hydroxy acid) or a salt or a lactide thereof;
wherein the at least one imidazoline amphoteric surface-active agent is a compound of formula (I):

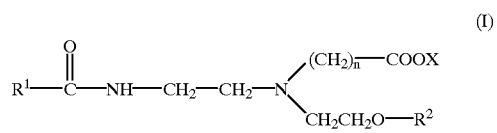

in which:
R¹ represents a saturated or unsaturated hydrocarbon radical,
R² represents a hydrogen atom or the group —(CH$_2$)$_m$—COOY,
X and Y represent, independently or simultaneously, a hydrogen atom or a monovalent cation,
n is an integer equal to 1 or 2 and
m is an integer equal to 1 or 2.

26. A detergent hair composition comprising a cosmetically acceptable medium containing:
(a) at least one anionic surface-active agent;
(b) at least one imidazoline amphoteric surface-active agent;
(c) at least one conditioning agent; and
(d) at least 2% by weight relative to the total weight of the composition of at least one carboxylic acid having a hydroxyl radical in the α-position (alpha-hydroxy acid) or a salt or a lactide thereof,
wherein the at least one imidazoline amphoteric surface-active agent is a compound of formula (I):

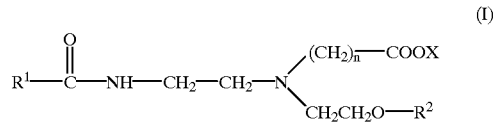

in which:
R¹ represents a saturated or unsaturated hydrocarbon radical,
R² represents a hydrogen atom or the group —(CH$_2$)$_m$—COOY,
X and Y represent, independently or simultaneously, a hydrogen atom or a monovalent cation,
n is an integer equal to 1 or 2 and
m is an integer equal to 1 or 2, and
wherein said component (d) imparts to said hair an improvement in at least one property selected from untangling, styling and softness,
compared to said at least one property that would be imparted to said hair by a composition differing only in that it does not contain said amount of said component (d) or does not contain said component (d) at all.

27. A detergent hair composition comprising a cosmetically acceptable medium containing:
(a) at least one anionic surface-active agent;
(b) at least one imidazoline amphoteric surface-active agent;
(c) at least one conditioning agent; and
(d) at least 2% by weight relative to the total weight of the composition of at least one carboxylic acid having a hydroxyl radical in the α-position (alpha-hydroxy acid) or a salt or a lactide thereof, wherein said at least one carboxylic acid is a linear α-hydroxy acid with less than 5 carbon atoms or an aromatic α-hydroxy acid, and further wherein the at least one imidazoline amphoteric surface-active agent is a compound of formula (I)

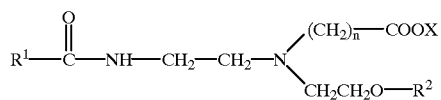

in which:
R$^1$ represents a saturated or unsaturated hydrocarbon radical,
R$^2$ represents a hydrogen atom or the group —(CH$_2$)$_m$—COOY,
X and Y represent independently or simultaneously, a hydrogen atom or monovalent cation,
n is an integer equal to 1 or 2 and
m is an integer equal to 1 or 2.

* * * * *